(12) United States Patent
Colburn, Jr.

(10) Patent No.: US 6,484,652 B1
(45) Date of Patent: Nov. 26, 2002

(54) SOIL CONSTITUENT SENSOR AND PRECISION AGRICHEMICAL DELIVERY SYSTEM AND METHOD

(75) Inventor: John W. Colburn, Jr., Houston, TX (US)

(73) Assignee: Crop Technology, Inc., Bandera, TX (US)

(*) Notice: Subject to any disclaimer, the term of this patent is extended or adjusted under 35 U.S.C. 154(b) by 0 days.

(21) Appl. No.: 09/699,795

(22) Filed: Oct. 30, 2000

Related U.S. Application Data

(63) Continuation of application No. 08/944,843, filed on Oct. 6, 1997, now Pat. No. 6,138,590, which is a continuation of application No. 07/733,442, filed on Jul. 22, 1991, now abandoned.

(51) Int. Cl.[7] .............................................. A01C 23/00
(52) U.S. Cl. ........................ 111/118; 111/903; 111/200; 111/121; 47/1.3; 204/400; 324/347
(58) Field of Search ................................ 111/118, 200, 111/900, 903, 904, 121; 172/1, 2; 47/1.3; 73/73, 763; 175/50; 204/400

(56) References Cited

U.S. PATENT DOCUMENTS

| 3,581,197 A | * | 5/1971 | Morey, Jr. et al. |
| 3,999,121 A | * | 12/1976 | Taylor, Jr. ................ 324/65 CR |
| 4,095,169 A | * | 6/1978 | Muse ............................ 324/8 |
| 4,219,776 A | * | 8/1980 | Arulanandan |
| 4,646,000 A | * | 2/1987 | Wills |
| 4,654,598 A | * | 3/1987 | Arulanandan et al. |
| 4,693,419 A | * | 9/1987 | Weintraub et al. |
| 4,931,775 A | * | 6/1990 | Sheriff ........................ 340/604 |
| 5,033,397 A | * | 7/1991 | Colburn, Jr. ................ 111/118 |
| 5,407,134 A | * | 4/1995 | Thompson et al. ......... 239/156 |
| 5,673,637 A | * | 10/1997 | Colburn, Jr. et al. ....... 111/118 |
| 5,841,282 A | * | 11/1998 | Chrity et al. ................ 324/347 |
| 6,138,590 A | * | 10/2000 | Colburn, Jr. ................ 111/118 |

FOREIGN PATENT DOCUMENTS

EP          0370593      *  5/1990

* cited by examiner

*Primary Examiner*—Victor Batson
(74) *Attorney, Agent, or Firm*—D. Arlon Groves

(57) ABSTRACT

A real time soil constituent sensor and precision agricultural chemical delivery system may measure simple in situ soil constituents without the aid of externally applied solvents, or such solvents may be utilized intermittently to calibrate the measurements for greater accuracy. A real time complex in situ soil resistivity sensor and prescription agricultural chemical delivery system includes a plurality of ground-engaging tools in association with individual soil electrode arrays which measure complex solute and matrix resistivity levels. Conventional engaging tools may serve as electrodes for impressing a voltage source and serve as a current sink for the purposes of determining complex resistivity values and components thereof in in situ soils. Alternatively, local resistivity measurements in a single tool can also be employed for separation of resistivity cotributions of the soil solute and the matrix. For calibration, to enhance the accuracy of in situ measurements of matrix resistivity, a plurality of reference fluids of known conductivity are periodically injected at the interface between electrodes on a single tool and the in situ soil. A real-time soil solute and matrix sensor and controller senses and separates the resistivity contributions of the solute and matrix and compares these components against target levels or schedules and adjusts a servo-controlled delivery system to apply the appropriate amount of agricultural chemical substantially in the location from which a calibrated complex soil resistivity measurement was taken.

29 Claims, 11 Drawing Sheets

SOIL CONSTITUENT SENSOR AND PRECISION AGRICHEMICAL DELIVERY SYSTEM AND METHOD

This application is a continuation of U.S. patent application Ser. No. 08/944,843 filed Oct. 6, 1997 now U.S. Pat. No. 6,138,590, which was related to U.S. patent application Ser. No. 08/144,786 filed Oct. 29, 1993, which was a continuation of then U.S. patent application Ser. No. 07/733,442 filed Jul. 22, 1991, now abandoned, which was related to then U.S. patent application Ser. No. 07/562,210 filed Jul. 31, 1990, which was related to then U.S. patent application Ser. No. 07/275,266 filed Nov. 23, 1988 which was related to then U.S. patent application Ser. No. 07/076,055 filed Jul. 21, 1987.

BACKGROUND OF THE INVENTION

The present invention relates to an improved agrichemical system and method and, more particularly, to a system capable of sensing in real time the chemical condition of the soil and/or certain non-chemical parameters of interest such as organic matter, soil type and the like. This information may be utilized in real time to apply an appropriate amount of corrective agrichemical in response to a sensed deficit or excess or in response to the sensed non-chemical parameter while the apparatus is still traversing the soil sampled, or the information may be stored for later use or telemetered to a remote location. The system has important benefits in cost reduction, energy resource conservation, crop production, and reduction of environmental degradation.

Prior to the invention of U.S. Pat. No. 5,033,397 to Colburn, the modern farm practice of applying chemicals to the soil to obtain optimal crop yield differed little from that used a hundred years ago, when manure from farm animals and so-called "green manure" (composed of luguminous crops or harvest detritus) were added. The farmer, as always, desires sufficient soil fertility to ensure that a successful harvest will result from his planting. The methods by which the farmer's objectives are met have advanced considerably. Cropland productivity is increased many-fold with the application of specific chemical materials tailored to precisely provide the plant nourishment or protection needed. Beyond the need for adequate fertility, the crop is usually also given protection from competing weeds and insects by the application of assorted herbicides and insecticides. The recommended rates of application for many of these chemicals often vary as organic matter and soil type vary.

Fertilizers and agricultural chemicals are applied by diverse types of field equipment, including granular spreaders, liquid spray bars, and anhydrous solution, or granular injectors. Farmers also make choices as to when to apply the fertilizer for the next growing season, such as in the late fall or early spring, while planting, or after planting. Similarly, agricultural chemicals such as herbicides are applied at an appropriate stage of weed growth most likely to destroy or regulate undesirable plant growth.

Assorted variables influence the amount of nitrogen and other nutrients that are available for plant growth and development. In the case of nitrogen, local field conditions determine the quantity of ammonium held on the exchange complex of the soil and the precise mechanics of conversion to more available forms via bacterial action. Conversion of variable ammonium levels at distributed oxidation levels in soils is highly variable from point-to-point even within fields which appear relatively homogeneous. Although this extreme variability of soil chemical levels has been known since at least the 1920's, until the previous Colburn invention no one has perfected a method of accounting for this variability while adding fertilizers or other corrective chemicals such as lime.

As taught in Colburn U.S. Pat. No. 5,033,397, nitrogen exists in the soil in a variety of chemical forms. In the ammonium form it is relatively immobile, but after transformation by soil bacteria to nitrate its mobility increases drastically. Nitrate becomes elusive because of its high solubility in soil water. Nitrate moves with the soil water in response to soil temperature changes, rainfall, and crop transpiration demands. The coefficient of variation of soil nitrate levels typically has a mean of 50% and often reaches 100% even over small areas of only several square yards. Similar observations have been made for pH and potassium levels. Because available nitrogen varies widely, even when fields have been uniformly fertilized, sporadic, conventional soil samples cannot be representative indicators of a field's nitrogen availability status.

Insufficient nutrient or herbicide levels will affect crop productivity adversely; excess levels may have a similar effect, may carry over to affect the next crop or may simply be wasted. In a field of varying organic levels and soil types, the manufacturer's recommended rate of herbicide application would also vary but the farmer would typically be unable to vary his actual application rate in response to such variations. Farmers encountering such situations would have to utilize a constant application rate, and would typically select the highest of the various recommended rates and apply that rate of agrichemical uniformly across the field, with the aforementioned consequences. In the case of nitrogen, soil nitrate ($NO_3$—N) levels above 40 ppm are considered to be wasted nutrients. Field data indicate that considerable excess nitrate is often available that does not contribute to crop production. Because nitrate is mobile and does move downward away from the rooting zone in the absence of a crop, nitrate in the soil at the end of a growing season may not be available to the next year's crop but may serve only to contaminate ground water.

Plants use only those nutrients they need and the use of the nutrients complies with a law of diminishing returns. Above a certain threshold level, the farmer obtains little yield response with increasing nutrient level. From an energy efficiency perspective, nutrients applied above this threshold level are wasted. In the case of a normal distribution with a large coefficient of variation (ratio of standard deviation to the mean value), approximately 50% of the nutrients are wasted. This means that both the energy and raw materials used to manufacture the nutrient, as well as the farmer's profit dollars, have been squandered.

For example, nitrogen in its gaseous form is of no use to plants. Plants require that nitrogen, in the form of complex nitrogen compounds, be further transformed into soluble nitrates in order to be utilized by the plants. All agricultural chemical compounds, including manure, are toxic to some extent and can contaminate groundwater, particularly those in the nitrate form. Thus amounts of fertilizer greatly in excess of what the plants can profitably use cannot be prudently applied. They are also expensive, which is another good reason to not overfertilize cropland. Until the previous invention, the farmer had no practical way to optimize his application rate, nor to vary his application rate in response to changing conditions across his field. He had been limited to simply applying what worked in the past, perhaps aided by his recollection of how last year's crop came out, perhaps supplemented by a few spot soil analyses made around the field.

Because of the spatial variations in his field, and because of the time delay between sampling and receiving results—during which the soil conditions will have changed—the farmer who has paid for spot samples is scarcely better able to fertilize his fields than is the farmer who simply fertilizes on an historic basis. Consequently, farmers routinely apply excess fertilizer as a protective measure, and in doing so lower their profit margin and risk groundwater contamination, neither of which is desirable.

Farmers know, qualitatively, that crop yields vary because uniformly applied fertilizers are not converted uniformly to forms useful to plants. Farmers generally use rules of thumb to guide application timing. Moreover, farmers realize that their primary source of agrichemical recommendations beyond accepted rules of thumb is either an extension agent or a chemical sales representative.

Soil sampling, used to aid the farmer in fertilizer application, is conventionally based on a farmer's own sample timing and site selection rationale. Chemical analyses of soil samples that the farmer provides to the extension system agent or salesman require interpretation by technically trained personnel to reveal nutrient needs. Often, however, either no nutrient analysis is performed or the analysis is ignored as meaningless due to the perceived complexity of the technical issues in agricultural chemical management. Today, most generalized nitrogen management recommendations are based on experimental evaluation of different fertilizer treatment methods. Soil tests are not routinely done for available nitrogen at the farm level, and the "turnaround" time between sampling and receiving laboratory results is too long to satisfy the farmers needs for the timing of his application. Local, spatial variations which have significant effects on the crop are normally not addressed at all.

Accordingly, significant energy waste occurred in the application of agricultural chemicals simply because no proven, economical method existed to properly and timely allocate chemicals to meet crop needs, and agricultural chemicals and fertilizers were consequently applied in substantially uniform amounts irrespective of local variations in soil chemical conditions.

In summary, the conventional method of providing agrichemical recommendations for farm level chemical application includes soil sampling by the farmer himself and laboratory analyses, resulting in technically informed interpretations by technically trained personnel. These recommendations normally are then implemented—days or weeks later—by the farmer himself, who usually is not technically trained in these disciplines.

There are significant sources of error in this multi-step process, including, for example, errors unavoidably caused by the time delay and errors in selecting a truly representative sample, sample collection and handling, sample preparation and conditioning in the laboratory, trained interpretation of nutrient or other chemical needs, and errors in application of the recommended level due to the imprecision of the chemical application equipment.

SUMMARY OF THE INVENTION

In a simple form of the invention, and under the proper circumstances, the apparatus and methods of Colburn U.S. Pat. No. 5,033,397 may be used to accurately determine soil deficit or excess conditions in real time, i.e., "on-the-go" while traversing a field, without the aid of a solvent for such measurements as taught therein. As the calibration factors disclosed therein will rarely remain constant over fields of any significant size, a first improvement to this recent discovery may be effected by intermittently utilizing the solvent distributing apparatus disclosed therein to update such calibration factors on a frequent basis. That is to say, in this, mode of operation the system may operate in a manner opposite to that disclosed in Colburn U.S. Pat. No. 5,033,397; i.e., potential and resistivity determinations may be made in the absence of any solvent, and solvent may be exuded solely for calibration purposes. Although one may store such information for use in the later addition of corrective chemicals, or telemeter such information or the directly measured information to another installation for subsequent use or processing, it is preferred to utilize such information in real time while traversing the sample actually measured to determine and apply the precise amount of agrichemical to the sample measured. In this manner the slight but highly significant positional errors inherent in such bifurcated techniques may be avoided entirely, as may changes in conditions due to the passage of time and the cost and inconvenience of a subsequent field operation.

Beyond the conditions for which the previous invention was intended, or for greater accuracy, it is preferable to measure the complex soil resistivity rather than just the 'simple' soil resistivity (or the teal component of the complex resistivity) as was done previously. It is a further improvement to measure the naturally occurring solute present in the soil, as well as proportional clay content and organic matter, and to utilize the latter to aid in applying chemicals in addition to soil correcting chemicals. In still another improvement, the measuring apparatus may be calibrated intermittently through the aid of either a fluid of two different conductivities or two different fluids of differing conductivities. Such fluid(s) may be of known conductivities or unknown conductivities. Additionally, such calibrating fluids may be "working" fluids, i.e., the same kinds of fluids being precision-applied to the reference field, such as herbicides and the like.

DESCRIPTION OF THE PREFERRED EMBODIMENT

The system of the Colburn U.S. Pat. No. 5,033,397 invention may be most advantageously employed in applying fertilizer or other corrective chemicals a few weeks after crop emergence. While such post-plant application has been demonstrated to be much more efficient than pre-plant application, it often is necessarily limited to a time duration of Just a few weeks. In many instances it would be desirable to be able to make such determinations without the use of the solvent taught therein, while in other instances it would be desirable to extend the time period during which the localized soil parameters of interest could be determined.

It has been discovered that in adequately moist soils of sufficient warmth, measurement of simple resistivity without the use of solvent remains correlated with available soil nitrate levels sufficiently to permit such measurement without the use of a solvent and a leachate. Preferably, soils being measured without a solvent and leachate will have a moisture content above the wilting point and, for convenience, will be dry enough to permit normal field operations. It is also preferable for the average soil temperature at a few inches depth to exceed approximately 50° F. Under these conditions, adequate correlation has been found to permit the efficacious use of the system without an externally applied solvent and resulting leachate.

Beyond these operating conditions, or for greater accuracy within these conditions, it has been found preferable to measure the complex soil resistivity, or impedance. In Colburn U.S. Pat. No. 5,033,397, measurement of resistivity utilizing both time-varying voltages and constant voltages was taught. In the present invention, either constant or time-varying voltages may be used as well, although when measuring complex resistivity it is preferable to utilize time-varying voltages. Also, when employing alternating current excitation, peak voltages are preferably held below about 1.2 volts in order to avoid electrode reaction complications resulting from electrochemical effects at electrode interfaces when measuring complex in situ soil resistivity. If a time-varying voltage is impressed across an electrode-soil system, the propagation of current by direct exchange of electrons is influenced by the complex resistivity or impedance of the system. Complex soil resistivity+ may be considered, by analogy to electric current analysis, as comprised of a real, resistive component (or 'simple resistivity' as used heretofore) and an imaginary, capacitive component of the impedance. If the voltage levels are kept below about 1.2 volts, the charging of the double layer of ions surrounding the electrodes in response to an applied alternating voltage will not produce the oxidation-reduction reactions of U.S. Pat. No. 5,033,397.

Thus complex resistivity includes as subclasses both the electrochemical slurry signal enhancements described in U.S. Pat. No. 5,033,397 at voltage levels appropriate to that subclass and the baseline resistivity signals at lower applied voltages resulting from in situ and solution imbrued soil electrical transmission.

In the present invention, a time-varying voltage regime is preferred since it may provide the most information from interrogation of in situ electrode-soil systems. In a non-steady state electric field, the current I passing through a conductive soil with capacitive reactance is expressed as the ratio of the instantaneous voltage V to the complex resistivity or impedance $Z_e$, or, in equation form, as:

$$I=V/Z_e$$

The complex resistivity or impedance $Z_e$ is itself expressed as:

$$Z_e=[r^2+(2\Pi f C)^{-2}]^{0.5} \quad [1]$$

where,

C=soil extrinsic capacitance=$\epsilon A/L$
$\epsilon$=soil intrinsic permittivity
r=soil resistivity=L/Ac and
c=soil extrinsic conductance
A=soil area for current flow
L=soil length for current flow
$\epsilon_r=\epsilon/\epsilon_o$, the dielectric constant of the soil, and
$\epsilon_o$=vacuum permittivity Soil pore fluid provides both a resistive (real) and a dielectric (imaginary) capacitive medium amenable to transient analysis methods, such as induced polarization or time domain reflectometry which permit soil conductance and dielectric constant values to be determined simultaneously. Alternatively, two or more widely separated excitation frequencies such as 1 KHz and 1 MHz or more can be used to determine the frequency dependence of the complex resistivity.

The benefit of using either of such methods is that the purely conductive component of impedance may be separated from the capacitive component by various circuitry and computational means familiar to those skilled in the electrical arts. The capacitive component has been determined to be functionally related to soil moisture content which is also diagnostically indicative of soil clay content and texture. The conductance component, along with knowledge of soil texture and particle conductance contribution, through heuristic rules or by the further methods herein disclosed, provides the necessary means for determination of representative soil solute levels. For example, if two excitation frequencies are used, the real component of the complex resistivity is not affected by a change in excitation frequency. Thus, two measurements of impedance at two different frequencies provide simultaneous linear equations from which both the resistive and capacitive properties can be extracted. Thus the dual measurements provide the measure of both conductivity (ECa) and water content ($\Theta_w$).

Recent works by J. D. Rhoades and others provides new formulations for interpreting the temperature-corrected real component of complex soil resistivity for analyses of soil solute levels. These models demonstrate the significance of soil structure and textural base on in situ conductance. The principal conductivity equation of interest to the present invention is given by the relation:

$$EC_a=EC_s+T\Theta_w EC_w \quad [2]$$

where $EC_a$=in situ measured conductivity
$EC_s$=soil Darticle conductivity
$EC_w$=soil solution conductivity
$\Theta_w$=soil water content (% wt. basis) and
T=Transmission coefficient Utilizing these models for determination of soil nitrate levels, for example, requires gain (T) and offset ($EC_s$) factors, each of which is determined by the textural characteristics of the soil and its mineralogy. Thus, these models can be efficiently used by external input of the factors or through independent sensory determination of soil texture such as by the "feel" method and soil particle conductance. In the preferred embodiment, calibration factors may be derived from one or several sources. For example, the relative influence of soil mineralogy on offset factors can be derived from surveys of local clay mineralogy. Such data provide information on relative changes in ground conductivity values that are dominantly influenced by conductive liquid imbibed conductivity characteristics of indigenous imbibed clay minerals, such as kaolinite, ⁻illite, montmorillonite, etc. Such regional characteristics may be input to the controller by the equipment operator or field service representatives. Alternatively, values can be precisely determined by direct comparative measurements of in situ solution imbrued soils. In this method, the soil pores are imbrued with solutions of two different conductivities. Two conductivity measurements respectively provide two simultaneous linear equations which can be solved for the values $EC_s$ and $T\Theta_w$. From, for example, the measurements of complex resistivity, as described previously, a value of $\Theta_w$ may be derived, allowing T to be determined by mathematical substitutions.

Thus, each parameter of interest can be derived from the combination of the equations of the components of the resistivity and the calibration methods described. Substituting these individual parameters reveals the in situ soil solution conductivity ($EC_w$). Since we have observed that soil solutions of midwest agricultural soils are dominantly composed of calcium and soluble nitrate ions (e.g. $Ca(NO_3)_2$), soil nitrate levels can be estimated from the measured conductivity relation for pure $Ca(NO_3)_2$ solutions. Alternatively, empirical relations obtained from extracts may be used, such as 10 meq/l of $NO_3^-$ produces an $EC_w$ value of 1000 micro S/cm.

It has been determined that soil particle conductivity is influenced by a soil's cation exchange capacity. The principal limitation on determining correlations with cation exchange capacity is that absolute values are difficult to assess since each laboratory's particular methods (e.g. soil grinding and extraction) influence the absolute value of the cation exchange capacity determined. On a regional basis, in a particular soil mineralogy and cropping history, cation exchange capacity has been confirmed to be an appropriately correlated parameter in the major agricultural area of the United States, the Corn Belt.

Cation exchange capacity arises from the negatively charged particle structure of soil colloidal clay minerals and soil colloidal organic matter. In general, the contribution of soil colloidal organic matter total cation exchange capacity dominates over the contribution of clay minerals in the surface soil layer (0-12") or the "A" (or plow depth) horizon. Indigenous clay minerals provide the dominant conductance influence at deeper horizons.

By using the methods of the present invention, the various components of in situ soil complex resistivity can be determined and related to soil parameters of interest for precision application. For example, in the mineral clays of central Illinois, in a silty clay loam with a water content of 20%, an $EC_s$ conductivity value of 0.40 mmho/cm would represent a CEC (cation exchange capacity) (Brookside Laboratories) of 25 meq/1 and an organic matter level of 4.4%.

By accounting for the soil particle cation conduction through calibration, the major calibration concern of additive conductive bias (offset) can be eliminated from the local complex resistivity measurement, leaving only the multiplicative bias (gain) of variation in water content for further calibration correction. Multiplicative bias in soil conductivity interpretation accrues through imprecision in assessment of the transmission coefficient. By measuring resistivity at sidedress or at planting time when soil moisture content is representative, multiplicative bias is minimized. Complex resistivity analyses can further reduce multiplicative bias, although with a quantitative determination of offset, empirical or heuristic regional relationships can be employed to determine the gain factors.

Complex resistivity methods of the present invention exploit both macroscopic and local interrogation of soils. In the methods herein described, the steady-state complex resistivity value may be determined by the following relation:

$$\rho = \frac{4\pi a R}{n} \quad [3]$$

where
 $\rho$=soil resistivity (ohm-meters)
 a=spacing between measuring electrodes
 R=resistance
 n=an empirical geometric factor Thus, although the value of the soil resistivity parameter is independent of the measurement methodology, the geometry of the system determines the resistance value to be measured in the sensing circuitry.

Local measurements between electrodes on the same ground-engaging tool ("a" measured in centimeters) necessarily create much higher resistance (R) values than do macroscopic measurements between tools on adjacent crop rows ("a" measured in meters). R is approximately two orders of magnitude lower in macroscopic measurements than in local measurements.

In the case of interpretation of nitrate levels, it is generally found that interrogation of the first foot of soil depth produces a value representative of the upper three feet and measures approximately 50% of the nutrient supplying capacity of the soil. Deeper interrogations provide means of locally interpreting the contributions, particularly for soil regions in which substantial conventional sampling has not been conducted.

Further, in some farming choices, fertilizers are band applied, such as anhydrous ammonia, starter, and manure. Separated electrode arrays offer the advantage that the contribution of bands to crop fertility can be measured by volume integration, rather than discrete sampling.

In the present invention, local resistivity measurements are preferably used in conjunction with the application of known conductivity imbruing soil solutions for calibration, and macroscopic multiple electrode methods are preferably utilized to provide locally averaged values of soil parameters determined from complex resistivity measurements. In the preferred embodiment, calibration of the improved soil resistivity sensor for soil particle conduction, e.g., from organic matter and clay cations, may be effected by linear extrapolation from 'two-fluid' resistivity measurements to the intercept.

It has been determined from agronomic studies of crop response to soil variables that both crop yield and quality are related to spatial variations of soil texture and chemical constituents. The spatial variation of soil clay content in a field influence crop uptake of nitrates, thus influencing crop quality. Further, soil type and textural characteristics have long been used by the USDA Extension system to rate the yield potential of soils. Existing regional recommendations of existing agricultural services may thus be used to assist in fertilizer application on the basis of a component of complex soil resistivity (e.g., $EC_s$ or T). Thus crop quality and production may be spatially influenced by treating a soil in response to those soil variables which are revealed through complex resistivety and solution calibration analyses. Multiple agrichemical treatments can simultaneously be prescribed from the sensory measurements of the system and method of the present invention.

Further, it has been observed that the primary limiting nutrients in most cropping situations are the $Ca^{++}$ and $NO_3^-$ ions. High $NO_3$—N levels are favorable to the extraction of calcium from the exchange complex of the soil. This is confirmed by the dominance of the calcium cation and the nitrate anion in soil solutions in the major agricultural region of the United States. Thus through $EC_a$, the contributions of $EC_s$ and $EC_w$ are combined into a fertility index of the major nutrients influencing crop yield.

IN THE DRAWINGS

Figure 8:
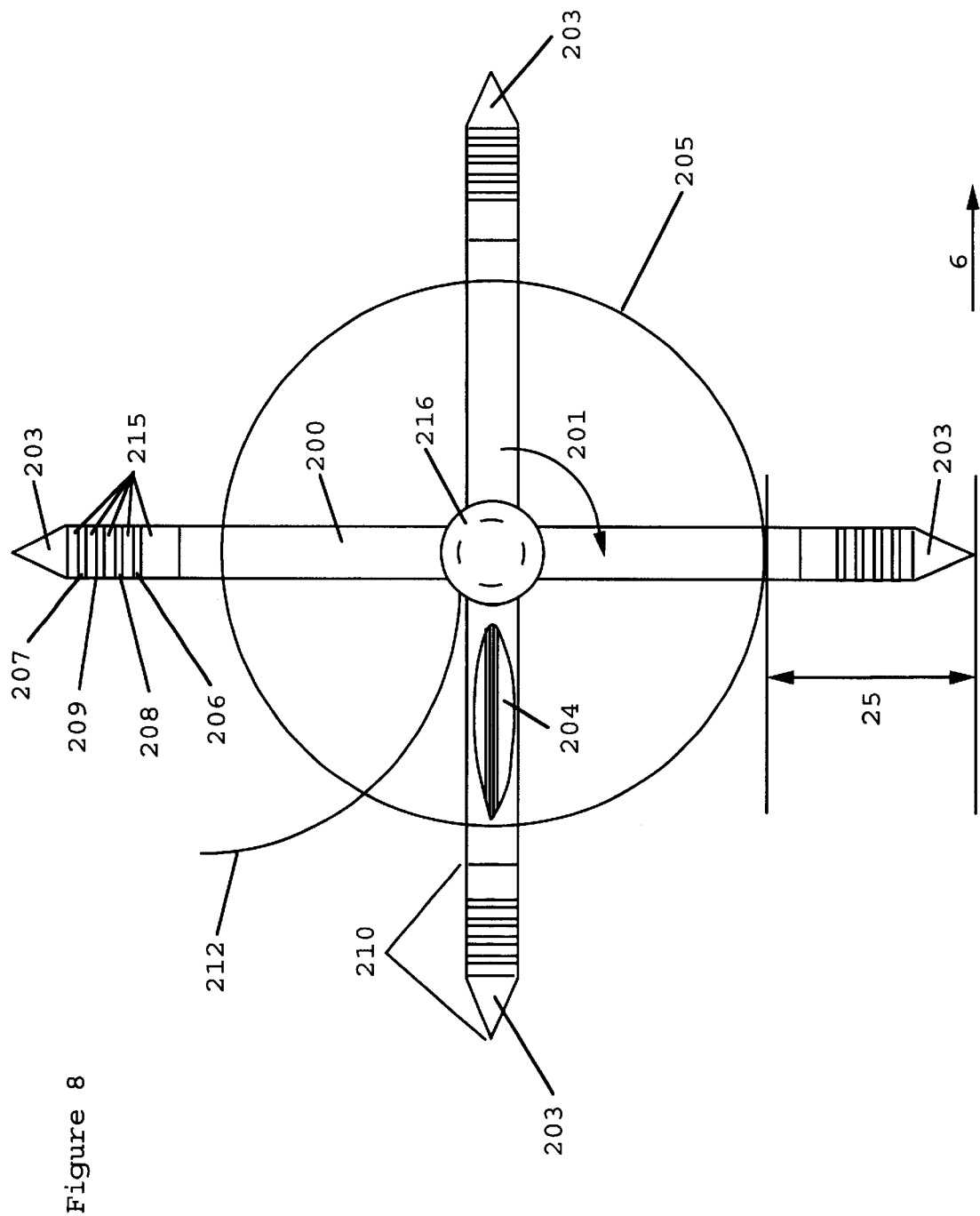

FIG. 8 portrays multiple four electrode annular arrays each radially attached to a rotatable spoked wheel.

Figure 9:
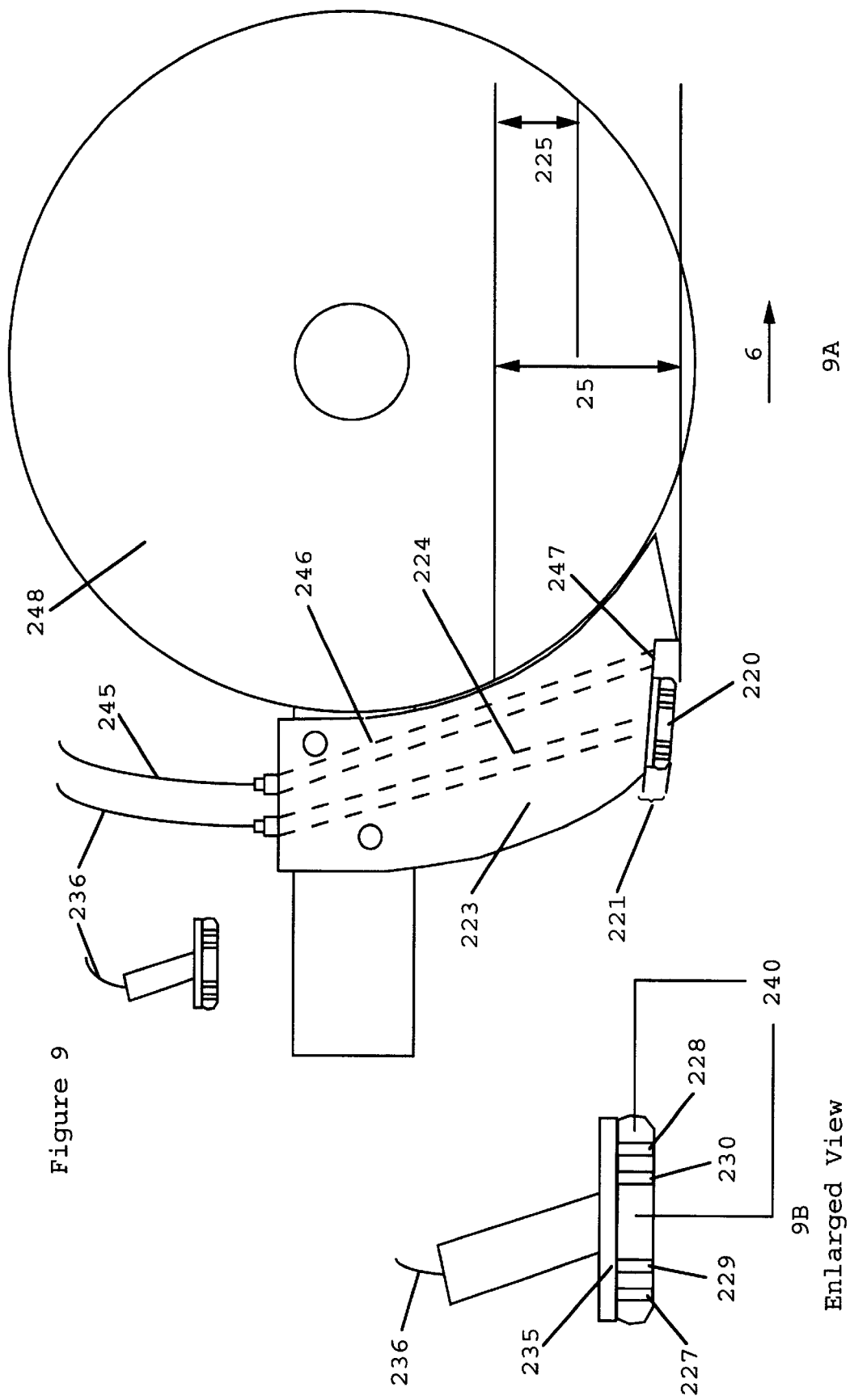

FIG. 9 depicts a removable four element array electrode attached in proximity to the heel of a ground-engaging knife.

Figure 10:
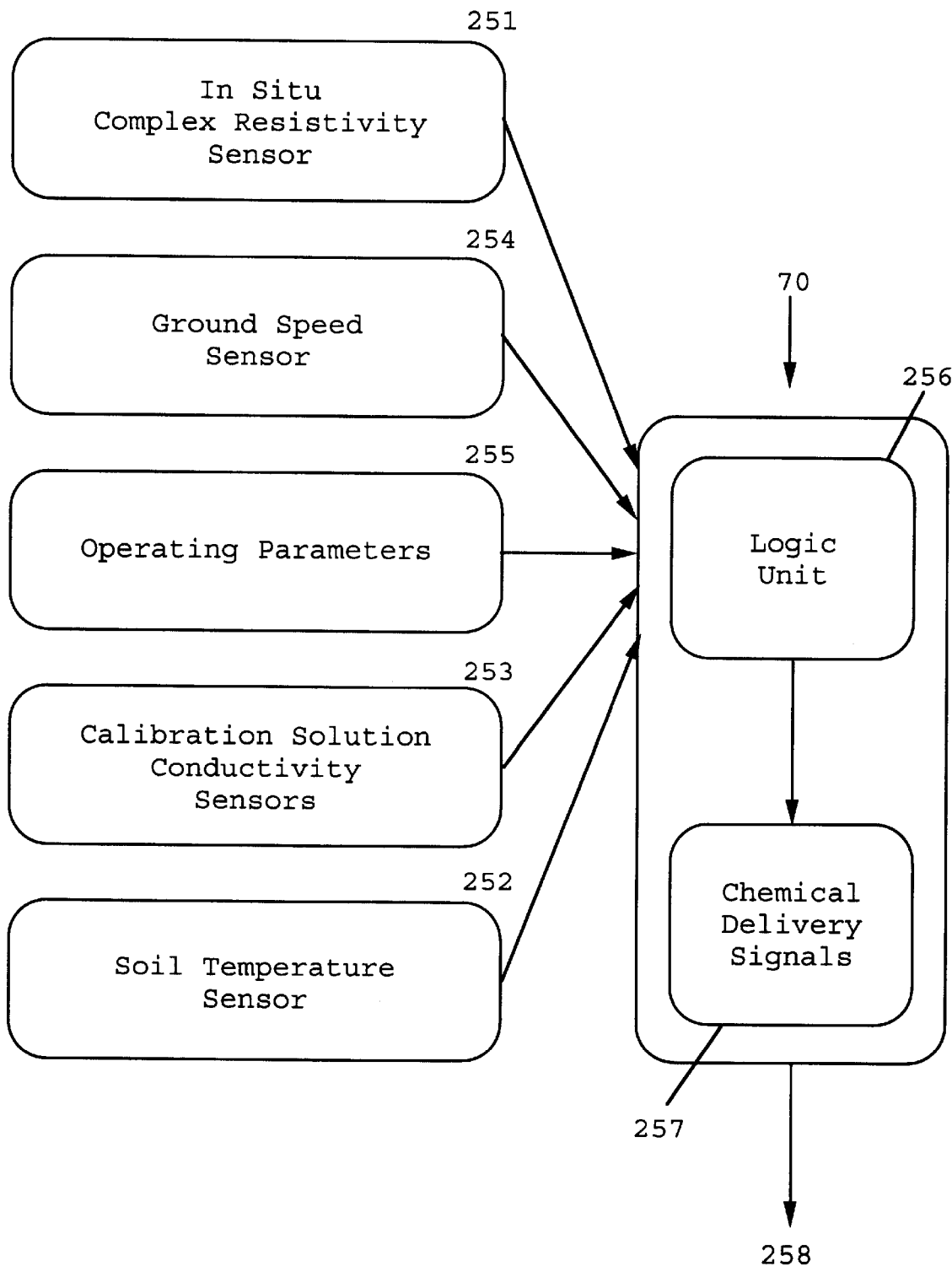

FIG. 10 is a schematic representation of the main sensory inputs, regional inputs, and command outputs of one system of the present invention.

DETAILED DESCRIPTION OF THE PREFERRED EMBODIMENT

It is to be understood that the soil solute and matrix sensor and agricultural delivery system of the present invention, when used to apply fertilizer, for example, may automatically, without tractor operator interaction, apply the needed chemicals to soil regions with low solute or matrix parameter values to bring them to proportionally higher values. For example, the matrix component of the resistivity may be utilized as an indicator of soil type, where the increase in matrix conductivity indicates the capacity of the soil to bind higher application levels of anhydrous ammonia, immobile P&K forms, or to require higher levels of herbicide for its indigenous organic matter. By further example, after adjustment of matrix effects, the influence of soil type on interpretations (gain factor) of the magnitude of solute resistivity can be decreased through isolation and interpretation of the capacitive reactance component of the complex resistivity.

Figure 1:
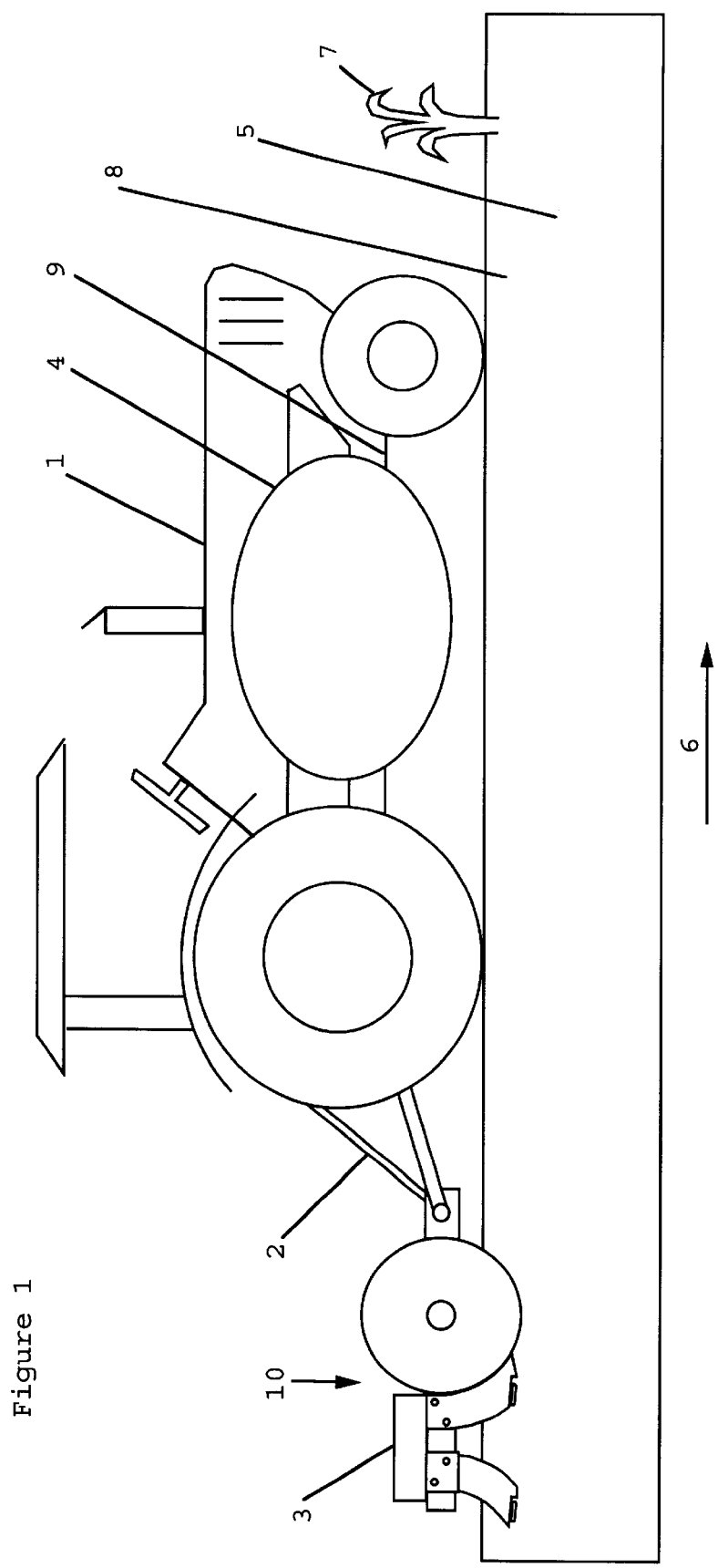
FIG. 1 is a simplified pictorial representation of a preferred embodiment of the system of the present invention in a typical field operation.

Referring now to FIG. 1, there may be seen a simplified pictorial representation of one type of system embodying the concepts of the present invention for sensing soil solute and matrix resistivity and dispensing the needed amount of corrective chemical. More particularly, there may be seen a farm chemicals application vehicle 1, commonly a farm tractor, flexibly and removably attached by adjustable lifting means 2, commonly a three-point hitch, to sensing and dispensing system 10. The resulting assemblage is shown being operated in direction 6 over farm soil 5 in which crops 7 are grown and measuring and calibrating the complex solute and matrix resistivity 8 of soil 5 and by determination by sensing and control means 3 supplying corrective farm chemicals withdrawn from a reservoir 4 removably attached to the frame 9 of the application vehicle. Crops 7 may include row crops, grasses, orchard crops, vineyards, or any other type of crop in which a mobile vehicle can routinely traverse the field and for which an appropriate soil solute or matrix resistivity level may be known.

Figure 2:
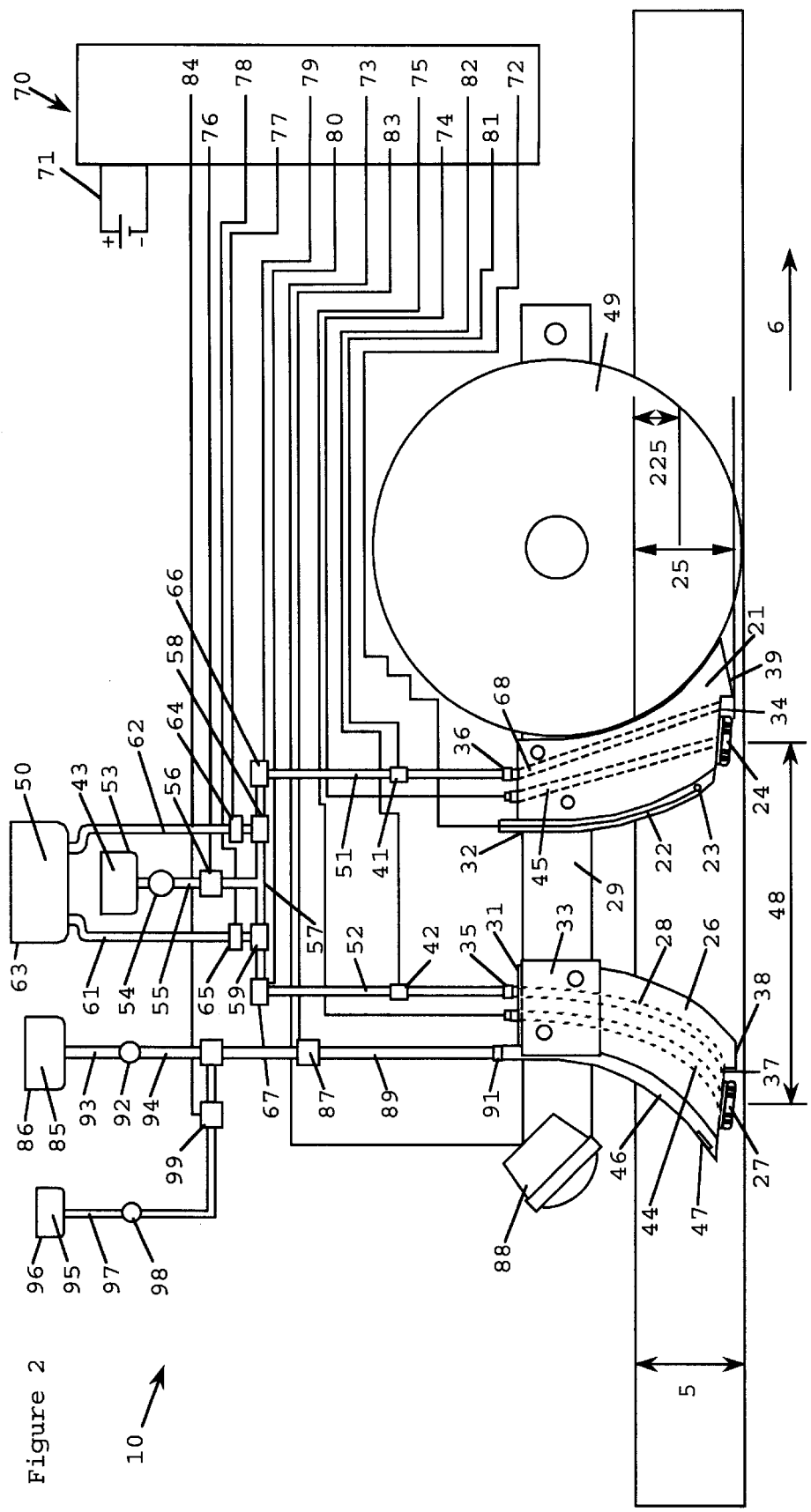
FIG. 2 is a functional representation of the preferred embodiment of the complex resistivity sensing and chemical application system.

Referring now to FIG. 2, the complex resistivity sensor and agrichemical control and delivery system 10 includes a first ground-engaging tool 21 incorporating a conduit 22 protected soil temperature sensor 23. Said tool may take many different forms, such as a knife, harrow, cultivator tine or the like, but will normally penetrate the soil 5 to bring a measuring electrode array 24 and the tool 21 to a desired depth 25. In proximity to the first tool, a second ground-engaging tool 26 may also be operated to penetrate the soil and bring an electrode array 27 to desired depth 25. Conductive electrodes of the measuring electrode arrays 24 and 27 may preferably be constructed of monel or stainless steel for corrosion resistance to calibration fluids passing therethrough. Ground engaging tools 21 and 26 are preferably narrow, thin, and may be tapered or oriented in non-parallel alignment to the direction of travel by adjustable mounting means 31 and 32 to facilitate soil penetration and to provide a minimum of soil fracturing in proximity to the measuring electrode arrays 24 and 27. Adjustable mounting means 31 and 32 are further adjustable vertically to permit changes in the mounting of tools 21 and 26 to accommodate wear of the tools and to preserve the preselected depth 25.

In both conventional and no-till farming, it has proven desirable to include a leading coulter 49 to provide an unencumbered path in the presence of residual surface crop debris or undecomposed root structures. It has been found that parallel linkage designs of coulters and trailing tools such as those produced by Yetter Manufacturing, Inc. of Colchester, Ill. are preferable to maintain the preselected depth 25 desired for the electrodes. The measuring electrode arrays 24 and 27 are preferably of the embodiment further shown in FIG. 9 and held to the bottom of the kerf created by tool or coulter passage but are removably affixed for wear replacement and electrically isolated from the ground-engaging tools as described herein below.

Figure 7A:
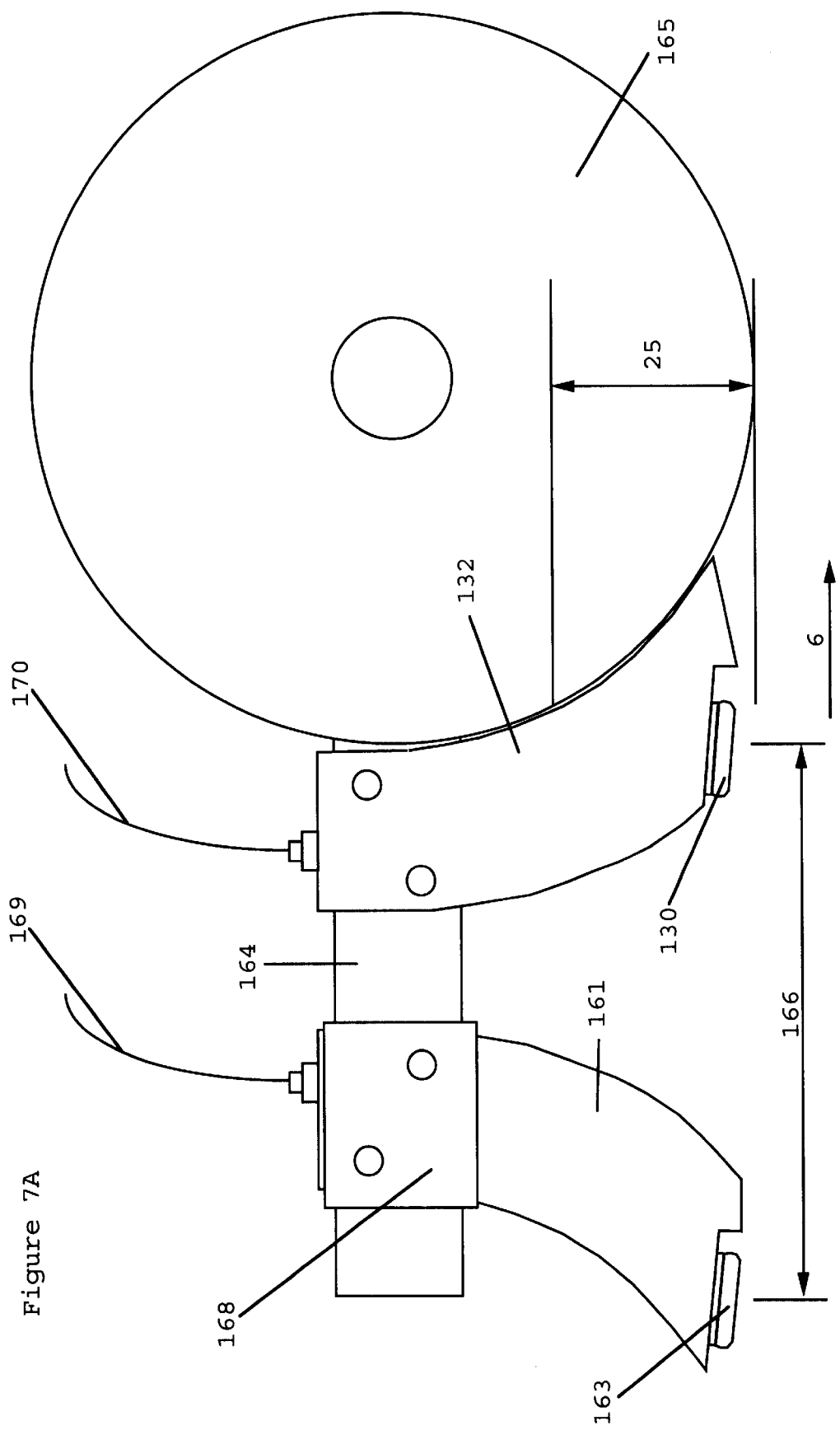
FIGS. 7A and 7B depict still other embodiments of separated electrode arrays.
Figure 7B:
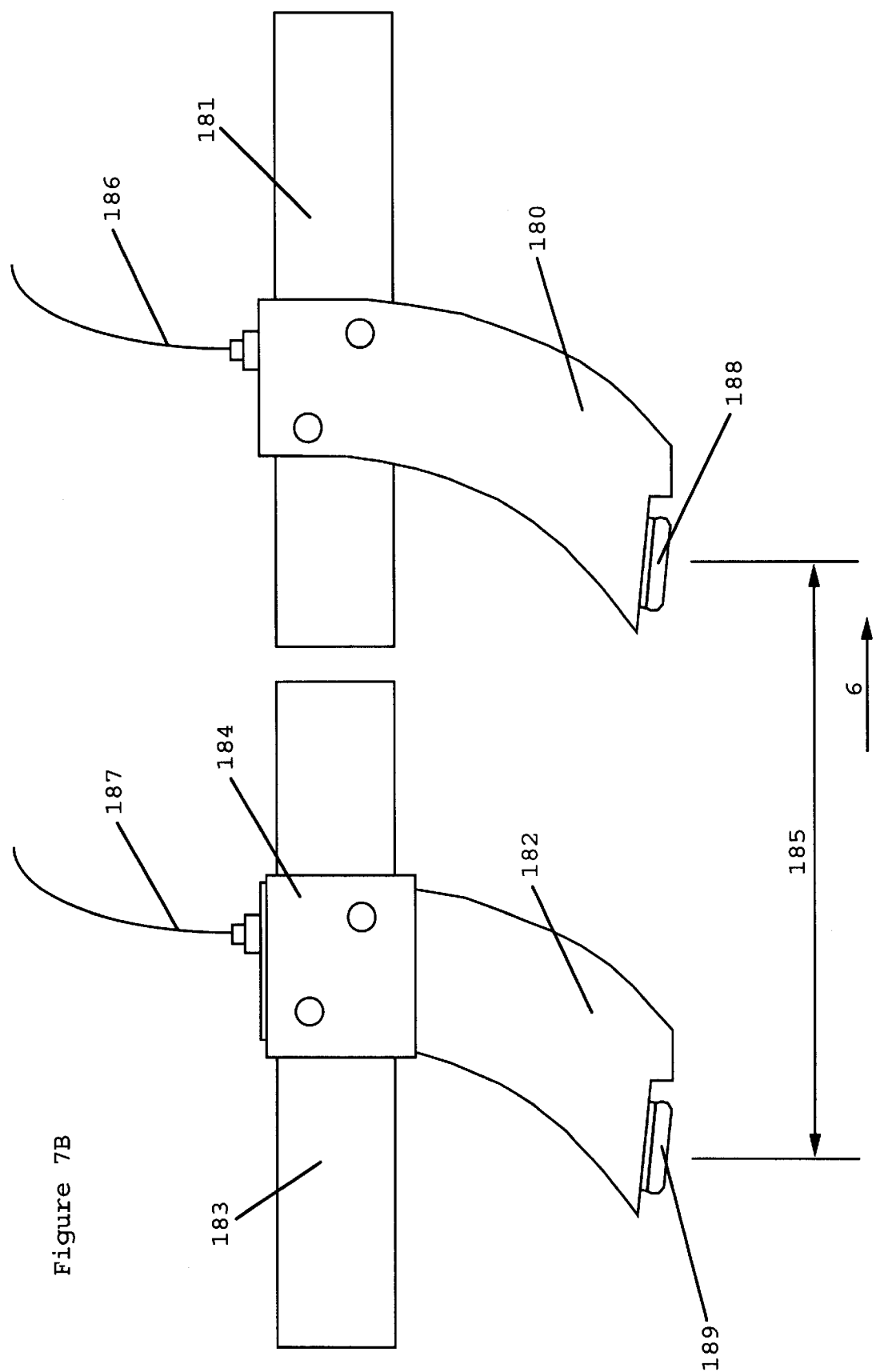

In the preferred embodiment shown in FIG. 2, complex resistivity values may contemporaneously be determined between the local measuring elements of the measuring electrode array 24 affixed to a first ground-engaging tool 21 and by means of current and potential measurements between the local elements of a first electrode array 24 and a second measuring electrode array 27 affixed to a second ground-engaging tool 26 operated on an adjacent crop row or at a known lateral or longitudinal distance from the first ground-engaging tool, as further illustrated in FIGS. 7A–B.

Figure 4:
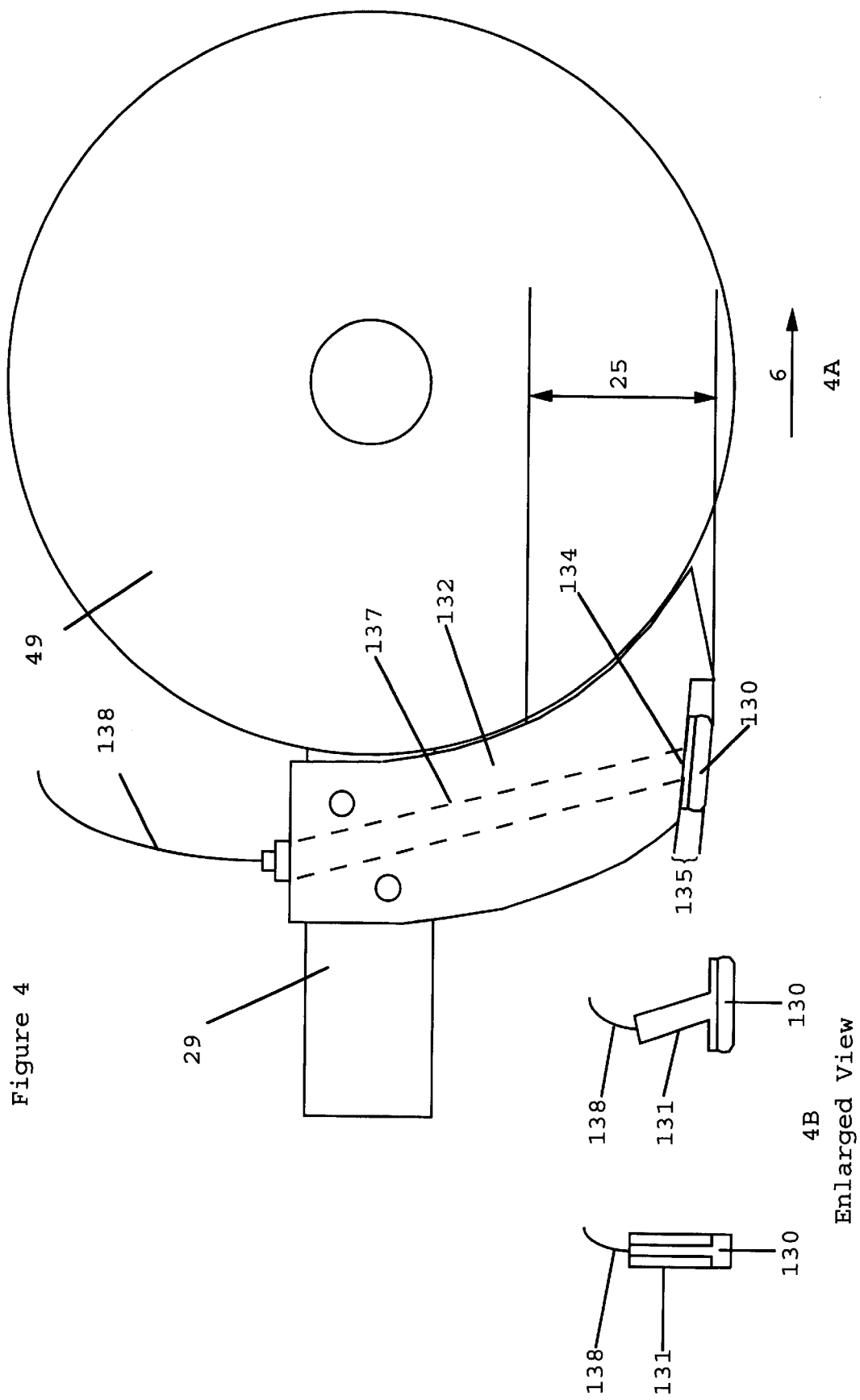
FIG. 4 depicts an alternate integrated, two electrode ground-engaging soil sensor in which the measuring electrode is removably affixed in proximity to the heel of the ground-engaging tool to afford maximum soil contact at the bottom of the kerf and soil fracture zone created by the passage of the tool.

In the preferred embodiment, a first 21 and second 26 ground-engaging tool may be formed of a conductive material such as iron, and one tool may serve as the positive voltage source when insulated from the frame 29 by insulation means 33 and the other tool may serve as the ground potential electrode for macroscopic resistivity measurements without imbruing solution calibrations, the measuring electrode on the latter ground-engaging tool may preferably be of the type illustrated in FIG. 4.

Ground engaging tools 21 and 26 are connected by adjustable mounting means 31 and 32 to support member or frame 29 which, when coupled to chemical application vehicle 1 (FIG. 1) in motion, conveys the draft force necessary to move the system 10 longitudinally through the soil in the direction of arrow 6.

For matrix resistivity calibration purposes, at least one ground engaging tool is fitted with a pressurized solution orifice 34, preferably of stainless steel, that precedes the first measuring electrode array 24 and through which two known conductivities of a farm soil and crop compatible chemical, preferably such as a dilute aqueous solution of 28% N fertilizer, may be sequentially passed. The first measuring electrode array 24 first measures a soil sample imbrued with a first conductive solution 51 and the soil sample is then imbrued with a second known conductivity solution 52 and the resistivity is measured again by electrode array 27 in the presence of the second imbrued solution.

Known conductivity solutions may be employed in this calibration method, or, alternatively, the solutions may be prepared while the vehicle is moving and reference measuring electrode arrays 41 and 42 such as are available from Yellow Springs Instrument Company, Ohio, may be included in the solution lines to monitor conductivities of the solutions generated on-the-go. The baseline calibration solution 43, which may be 28% N fertilizer solution, may be supplied from a storage container 53 which communicates with pressure pump 54 via conduit 55. Downstream of pump 54 the base calibration solution 43, under pressure, flows to the inlet of flow control valve 56 which is preferably a fast response solenoid valve and therefrom through manifold 57. Mixing means such as eductors or venturis 58 and 59 mounted downstream of the solenoid valve 56 provide mixing of diluent liquid 50 which may be aqueous from conduits 61 and 62 drawn from the calibration solution reservoir 63 and supplied through conduits 61 and 62 by flow control valves 64 and 65.

In response to electrical signals from sensing and control means 70, the desired amount of each calibration solution 51 and 52 at tractor speed is released through valve means 66 and 67 through conduits 28 and 68, respectively connected to the ground-engaging tools 26 and 21, and therefrom to check valves 35 and 36 out to solution orifices 37 and 34 on the bottom of the respective ground-engaging tools 26 and 21. Preceding each orifice there may be a protrusion 38 and 39 to prevent clogging of the orifices and buildup of soil on the leading edge of-electrode arrays 27 and 24. A desirable amount of each calibration solution released for matrix calibration is approximately 300 ml/minute when the ground-engaging tool is moving in the direction 6 at 10 miles/hour. The two calibration reference solutions should preferably be selected or mixed so as to -provide -conductivities in the range of 5 and 10 mmho/cm. Alternatively, two different amounts of the same conductivity solution may be employed to provide contrasting resistivities.

The components of the removably affixed electrode arrays 27 and 24 are preferably constructed of monel or stainless steel and connected by conduits 44 and 45 protecting multi-conductor wiring means therein. The electrode arrays 27 and 24 are positioned rearward or behind solution orifices 37 and 34 such that as the ground-engaging tool advances in the direction of arrow 6, the wetted soil will make intimate contact with all the elements of each electrode array 27 and 24, an action enhanced by the depth of operation of the array at the heel of each tool.

A voltage or -current preferably at a first alternating current frequency and amplitude below 1.2 volts from control means 70 is impressed across the outermost elements of each array and a high impedance measurement circuit measures the potential difference induced between the two innermost elements of the array as further explained in the description accompanying FIG. 9. Simultaneously, the frequency separation means of sensing and control means 70 may impress a voltage or current at a selected second frequency and amplitude below 1.2 volts, between ground-engaging tool 21 and ground-engaging tool 26. Either of these tools may be insulated by insulation means 33 from the support member 29 to allow current flow in either direction. A high impedance measurement circuit using frequency separation means of sensing and control means 70 measures the potential difference induced between the innermost pair of electrodes on the electrode array 24, and the measuring electrode 27 on ground-engaging tool 26 as further explained re FIG. 9. Sensing and control means 70 determines the components of the complex resistivity from potential and current measurements of the outermost pair of electrodes.

The sensing system disclosed herein has, in the real and practical world, two significant advantages for improving the precision of on-the-go complex resistivity measurements. It is very fast acting, essentially instantaneous, and it is economical to implement. The system just described and the method of using it within the present invention are deemed novel in every sense.

As shown in FIG. 2, applicator tool 26, which may also serve as a component of the complex resistivity sensor, is preferably a tool of a backswept configuration and attached to support member 29 such that applicator shank 26 cuts through the soil following the first ground-engaging tool to about the same depth 25 as the first tool 21 and in approximate alignment therewith. Behind the soil penetrating end of applicator shank 26 is a conduit 46 and an orifice 47 through which fertilizer or other corrective chemicals may pass out into the soil. Said agricultural chemical 85 is stored in chamber 86 with the flow therefrom being controlled by flow control valve 87.

The control valve 87, preferably a fast acting solenoid valve, may be rapidly opened and closed in response to a modulated output signal, from sensing and control means 70. The sensing and control means first determines a component of the calibrated complex resistivity of the soil and the true ground speed of the farm vehicle by conventional speed detection means 88, preferably a non-contacting sensor, and then determines the amount of chemical additive to be applied to reach the level desired in the soil the sensing and control means 70 then signals the chemical application control valve 87 to dispense the appropriate amount of corrective chemical through conduit 89 and check valve 91 driven by the pressure from chamber 86, in the case of anhydrous ammonia, or by additional pump means 92, which may be a squeeze or peristaltic pump, installed between conduits 93 and 94, in the case of most agricultural chemicals, and into or onto the soil.

While corrective agrichemical 85 is being delivered to soil 5, a second agrichemical 95 drawn from storage reservoir 96 through conduit 97 may be metered by metering pump means 98 and control valve 99, preferably also a fast acting solenoid valve, into mixing means 101 which may be an eductor or venturi. This second agrichemical 95 may be used to dilute agrichemical 85 and may for example be water when agrichemical 85 is a herbicide so as to provide high pressure, low concentration diluted solutions when the preferred application means is a spray nozzle located at orifice 47. When corrective agrichemical 85 is a fertilizer, the second agrichemical may be chosen to vary the treatment of the soil in proportion to the components and interpretation of the complex resistivity of in situ soil 5. In the case of fertilizer application, agrichemical 85 may be a nitrogen fertilizer determined by analysis from sensing and control means 70 of the solute resistivity component of the complex resistivity, and the second agrichemical 95 may be potassium chloride determined by analysis from sensing and control means 70 of the matrix resistivity component of the complex resistivity.

The preferred operation of this system is as follows. Support member 29 is hitched to the rear of a draft vehicle 1 as shown in FIG. 1, and both the ground-engaging tool and the applicator tool are lowered so that they penetrate the soil to a similar depth, preferably less than twelve inches. As the tractor moves in the direction of arrow 6, member 29 is drawn forward and attached tools 21 and 26 slice through the soil. Protrusions 38 and 39 on tools 26 and 21 prevent soil from clogging solution orifices 37 and 34 as calibrating solutions imbrue the soil 5. A positive potential is supplied from sensing and control means 70 to tool 26 and a positive potential is applied to one of the outermost electrodes on each of the electrode arrays 24 and 27. Ground potential is applied to the tool 21, positive potential is applied to tool 26, positive potential is applied to one of the outermost electrodes on each array 24 and 27, all under the supervisory logic from sensing and control means 70. A current proportional to the complex resistivity of the in situ soil then flows between the elements of the electrode array 24 on tool 21 and 27 on tool 26 and between the first tool 21 and the second tool 26 which may preferably be on an adjacent crop row or laterally spaced 48 for operation in a wheat crop. For calibration purposes, sensing and control means 70 instantly generates required signals to drive control valves 56, 64 and 65 to dispense dissimilar conductivity calibrating solutions 51 and 52 into the soil intercepted by electrode arrays 24 and 27. Sensing and control means 70, using on-board frequency separation means for the resulting plurality of complex resistivity sensor signals, upon separation of the appropriate complex resistivity parameters instantly generates the required signals to drive control valves 87 and 99 and thus to dispense the appropriate amount of agrichemical through orifice 47 as said orifice passes the region where the soil was interrogated an instant previously.

In a preferred embodiment, soil solute and matrix resistivity sensing and the corresponding application of the agrichemical proceeds continuously as the tractor traverses the field, thus providing a novel system for concurrent localized and macroscopic resistivity testing and agricultural chemical application in real time. The system of the present invention provides a much higher density of samplings and corrections per acre than conventional procedures and a density that cannot be cost-effectively provided by conventional procedures.

Referring now to FIG. 10, which generally portrays the functions of sensing and control means 70, it may be seen that sensing and control means 70 is provided with five types of inputs. Preferably, rapidly varying field operation direct sensory data from a plurality of complex resistivity sensors 251 operated at various spacings providing complex resistivity parameters at known soil temperatures 252 in the presence or absence of known conductivity calibration solutions 253, and true ground speed data 254 from a single, generally non-contacting sensor, are measured electronically. Regional calibration parameters 255 indicative of major mineralogical or conductive conditions of soils on which the system and method are operated are provided to control means 70 preferably by direct key entry by an operator or by means of electronic communication such as digitally encoded data or direct analog voltages from external sources. Control means 70 interprets all sources of these data in its logic control unit 256, producing a series of chemical delivery signals 257 that are transmitted 258 to a plurality of chemical delivery valves and coordinated with the suite of complex resistivity measurements made along the path of the sensing tool and applicator.

Returning again to FIG. 2, the preferred operation of sensing and control means 70 during field operation is as follows. With a voltage source 71 derived from the mobile farm vehicle of FIG. 1, sensing and control means 70 first determines the soil temperature of the local soil from conventional temperature detection means 23 which may be a copper-constantan thermocouple installed in conduit 22 affixed to tool 21 and connected by wiring means 72 to sensing and control means 70. Contemporaneously therewith, non-contacting true ground speed means 88 connected to sensing and control means 70 provides true ground speed by wiring means 73. Contemporaneously, complex resistivity sensor electrode arrays 24 and 27 are excited and provide their signals to sensing and control means 70 through respective wiring means 74 and 75. In response to signals generated by control means 70, fast acting valve means 56, 64, 65, 66 and 67 through respective wiring means 76, 77, 78, 79 and 80 provide calibration solutions 51 and 52 to orifices 34 and 37. As these solutions flow in their respective conduits, solution conductivity sensors 41 and 42 connected by respective wiring means 81 and 82 provide calibration conductivity values to sensing and control means 70. Contemporaneously, sensing and control means 70, utilizing potential and current measurements, determines the solute and matrix components of the complex resistivity of both local and macroscopic soil volumes, the calibrated matrix resistivity value from imbrued solutions, and provides further interpretation based on regionalized or local input parameters 155 of FIG. 10. Instantaneously, upon interpretation of the components of in situ soil complex resistivity, sensing and control means 70 commands fast acting valve means 67 and 99 through wiring means 83 and 84 to deliver the required amounts of respective agricultural chemicals 85 and 95 to the soil.

Practical experience has shown that the first requirement of the sensing and control means is to respond to fluctuations in ground speed of the tractor. Agricultural chemical flow to each chemical applicator shank or spray nozzle therefore is preferably directly proportional to the true ground speed of the tractor.

Input set point parameters to control means include the desired maximum agrichemical application rate and corresponding resistivity values appropriate to specify that rate, and the system measures the complex resistivity and self calibrates under commands from the sensing and control means 70 periodically as the system traverses a field. Agronomic practice variables for maximum application rates and desired complex resistivity component levels are not expected to be constants over a farm field and may vary depending on other field variables such as the planting time of the particular crop of the hybrid variety grown in the particular field. These parameters are area-by-area farm production guidelines and do not fluctuate as widely as local soil resistivity values; consequently, these input factors can either be operator input or externally commanded or communicated to the logic unit and varied between field subregions. By comparing the measured complex resistivity levels and derivative factors to the desired levels, the sensing and control means determines if agrichemicals need to be added and adds them in proportion to the amount required by local soil solute and matrix resistivity properties. Because it is in no way desired to restrict the range of interpretation of the resistivity data and the benefits derived therefrom, this interpretation can take the form most appropriate to maximizing benefits.

In a preferred embodiment for herbicide use, a local or macroscopic herbicide application rate (or sublocal) is set by a recommendation factor established by the herbicide manufacturer and labeled on his product containers based on soil organic matter levels. Calibrated soil matrix resistivity values may be correlated with soil organic matter levels and serve as the appropriate sensory input for local determination of herbicide application rates. For example, the local herbicide application rate may be represented as:

$H_{local} = C_{manufacturer} \times O.M.$ (matrix resistivity)

The local or macroscopic application rate becomes the instantaneous required rate and the total chemical flow rate from the pump means is then determined by the geometric constants of the applicator and the crop planting and the true ground speed of the implement.

In a preferred embodiment, a local or macroscopic maximum potassium application rate is set by an interpretation of calibrated soil matrix conductivity levels for local cation exchange capacity (CEC). Such recommendation formulations are routine calibration interpretations for regional soil laboratories. By way of example, the maximum local application rate for potassium as determined by Brookside Laboratories, Illinois, is:

$$K_{local} = 140.8677 \, (CEC)^{0.3982}$$

where CEC is determined by the laboratory methods of that laboratory and local soil matrix conductivity values may also be correlated with the same procedures. Similar procedures may be used to specify anhydrous ammonia application on the basis of exchange capacity or textural characteristics determined therefrom.

Solute conductivity values may be obtained by first calibrating the matrix conductivity by the methods herein, using two or more dissimilar conductivity reference fluids. With matrix conductivity determined, transmission coefficients (T), correlated with matrix conductivity, when farm fields are near field capacity, permit the estimation of matrix conductivity, or separation of the resistivity term $T \, \Theta_w \, EC_w$ of equation (2) as a parameter correlated with crop response to applied nutrients. In the preferred embodiment, a local or macroscopic nitrogen fertilizer application rate (or sublocal) is set by first subtracting a local soil nitrate resistivity measurement $(NO_3^-)_{local}$ from the control setpoint $(NO_3^-)_{setpoint}$. Recommended nitrogen application rates for soils at nitrate on a mass basis value less than this setpoint are proportionately adjusted by the ratio of this difference to the control setpoint, where the setpoints are interpreted in terms of calibrated in situ matrix resistivity values derived from measurements by the system and methods of the preferred embodiment and equations (1) through (3). The delay between the time the agrichemical leaves a control valve and the time it reaches the soil is an important consideration for precision application. As taught in Colburn U.S. Pat. No. 5,033,397, minimizing flow passage lengths between the control valves and delivery orifices minimizes delay time effects. It has also proven beneficial to include check valves 35, 36 and 91 in FIG. 2 adjacent to their respective delivery orifices to insure that flow passages remained filled in the absence of pressure of their respective solutions.

In operation, it may be desired to time average soil resistivity signals at a 5 sample running average at approximately 25 samples/second when a tractor is moving at 10 miles per hour for complex resistivity interpretation and produce time-averaged flow conditions. It is an object of the present invention to provide geometric arrangement means for both local and macroscopic measurements of complex resistivity values which also provide average representative values over the region treated by the system and method herein disclosed.

The preferred embodiment may be used in many forms to assay the components of complex resistivity both with and without imbruing conductivity solution calibrations. It has been found that local agronomic practices of farmers and even those practices recommended by university and extension personnel provide such generous use of agricultural chemicals that even uncalibrated values of soil resitivity values are suitable as control variables for determining and controlling local application rates. However, as the absolute minimum level of agrichemical application becomes paramount for environmental quality, absolute resistivity calibration values will achieve even greater importance. For these future requirements, all components of the method for increasing the precision of determining and utilizing complex soil solute and matrix resistivity values should be employed, including soil temperature measurements as previously described.

Figure 3:
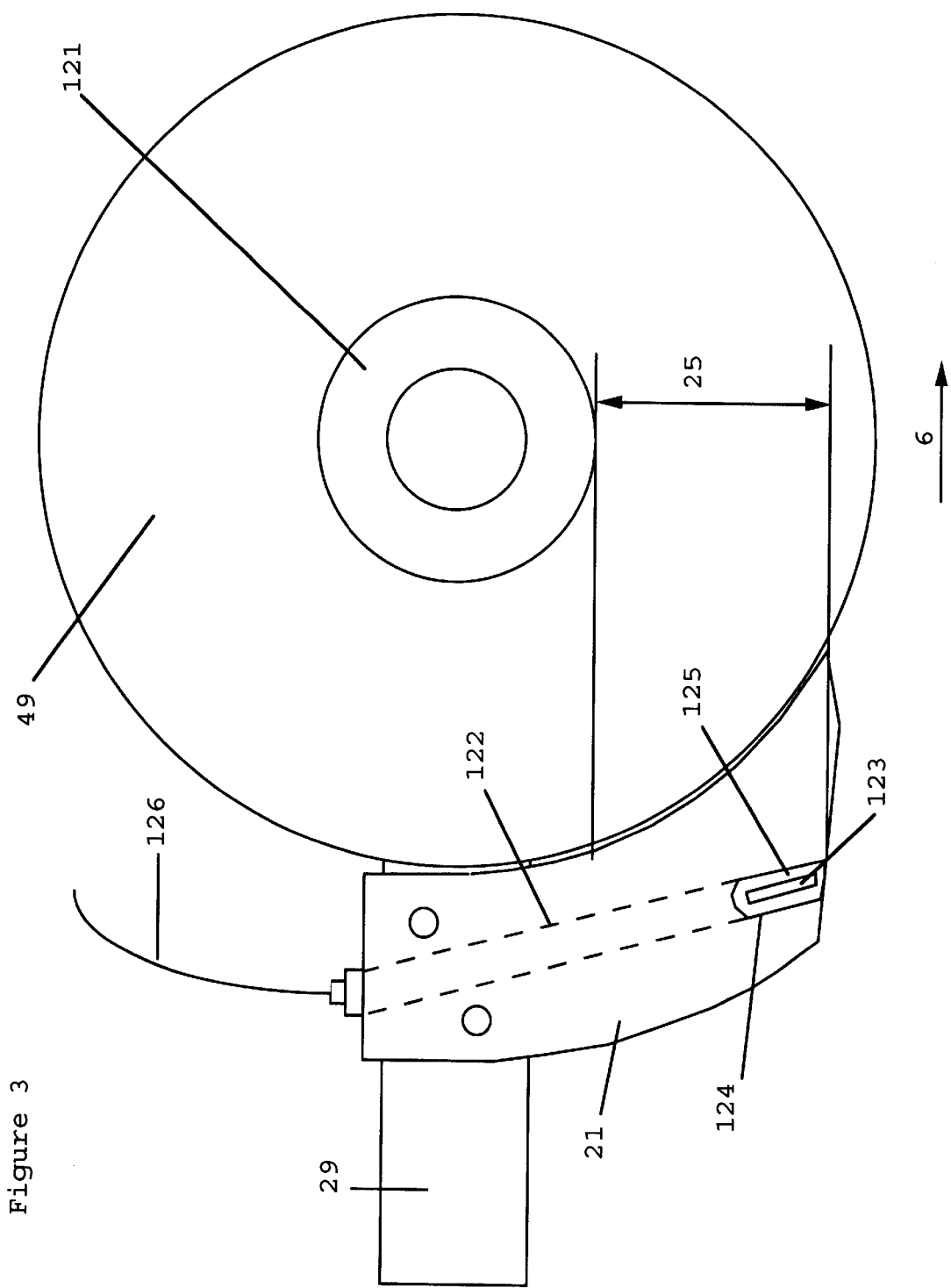
FIG. 3 depicts an integrated, two electrode ground-engaging soil sensor operated in conjunction with a coulter for unencumbered passage of the sensor electrodes through surface debris, stalks and roots, embodying additional mechanical means for increasing contact.

Referring now to FIG. 3, an integrated, two electrode ground-engaging complex in situ soil resistivity sensor is shown operated at a preselected depth 25 in conjunction with a coulter 49 for unencumbered passage in surface debris, stalks, and roots. The sensor is fitted with a preferably non-conducting kerf closing means, such as a wheel 121, which may preferably be in close proximity to the tool 21, to reform soil disturbed by tool or coulter penetration, thereby improving electrode-to-soil contact. The thin ground-engaging tool 21, which may be constructed of steel alloy and formed in a conventional crescent shape mounted to structural element 29 appropriately for use in conjunction with coulter 49, has integrated into its plane surfaces a flattened tube 122 into which is inserted a metallic measuring electrode 123 held at positive potential to the tool body 21 and preferably generally rectangular of ¼" width and 1" in length and insulated 124 approximately ¼" on all sides from the mounting aperture 125 and exposed to soil preferably on only one side of the tool 21. Tool 21 with its measuring electrode 123 is operated in the direction of travel 6 to assay in situ complex resistivity levels. Flattened tube 122 serves as a conduit for electrical cabling of excitation and signals. 126 to the control means 70 of FIG. 10.

Referring now to FIGS. 4A and 4B, an alternate integrated, two electrode ground-engaging in situ soil resistivity sensor is operated at a preselected depth 25 in conjunction with a coulter 49 for clearing surface debris, stalks and roots. The thin ground-engaging tool 132, which may be constructed of steel alloy of conventional crescent shape and mounted to structural element 29 appropriately for use in conjunction with coulter 49, has integrated into its surfaces a flattened conduit 137 into which is inserted a skid shaped or approximately "Tee" shaped metallic measuring electrode 130, held at positive potential to the tool body 132 and insulated 131 on all sides from the mounting aperture 134 and the interior of conduit 137 and from the tool 132. The measuring electrode 130 is preferably at least ¼" thickness in the plane of the tool 132 and is removably affixed for wear replacement and is oriented approximately in the direction of travel 6 below the heel 135 of the ground-engaging tool to afford maximum soil contact at the bottom of the kerf created by passage of the tool at depth 25. Flattened tube 137 serves as a conduit for electrical cabling 138 of excitation and signals to sensing and control means 70 of FIG. 10.

Figure 5:
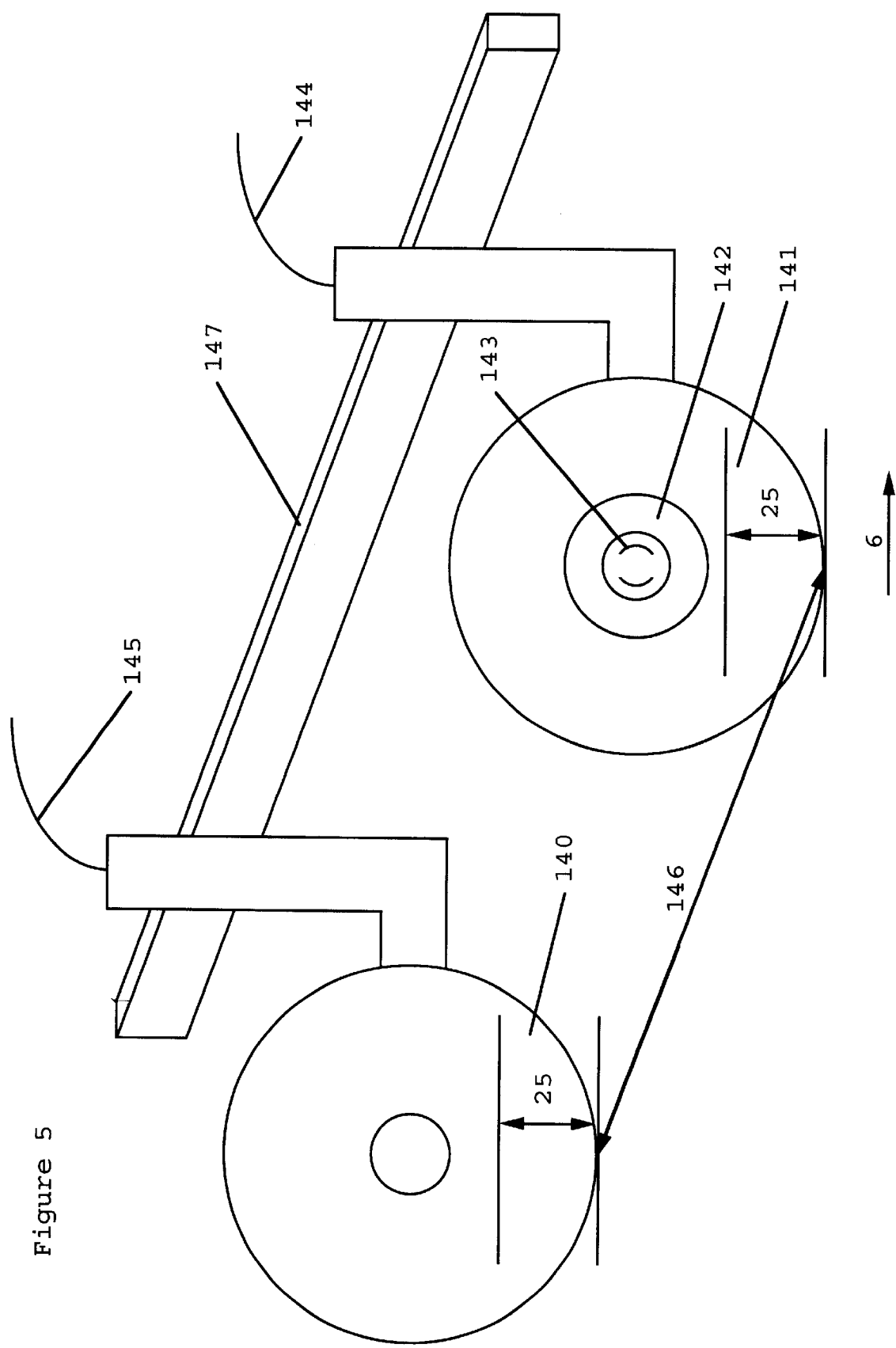
FIG. 5 depicts a two-electrode ground-engaging soil sensor configuration wherein each coulter serves as an electrode.

Referring now to FIG. 5, an alternate embodiment of a two-electrode ground-engaging in situ soil resistivity sensor includes two ground-engaging coulters as electrodes removably affixed to the implement 147 and operated at a selected depth 25 in direction 6 through the soil. Coulter 140 serves as the ground potential electrode by means of wiring 145 from control means 70 and coulter 141 is electrically insulated 142 from its hub save for electrical transmission means 143 such as slip rings to provide the driving potential by means of wiring 144 from control means 70 for current flow in the earth. This embodiment increases the volume of soil interrogated laterally 146 along an implement and simultaneously vertically into the soil in comparison to the micromeasurement afforded by the tool of FIG. 4 and is particularly suitable for commercial floater application of the sensing and control means 70 of the present invention.

Figure 6:
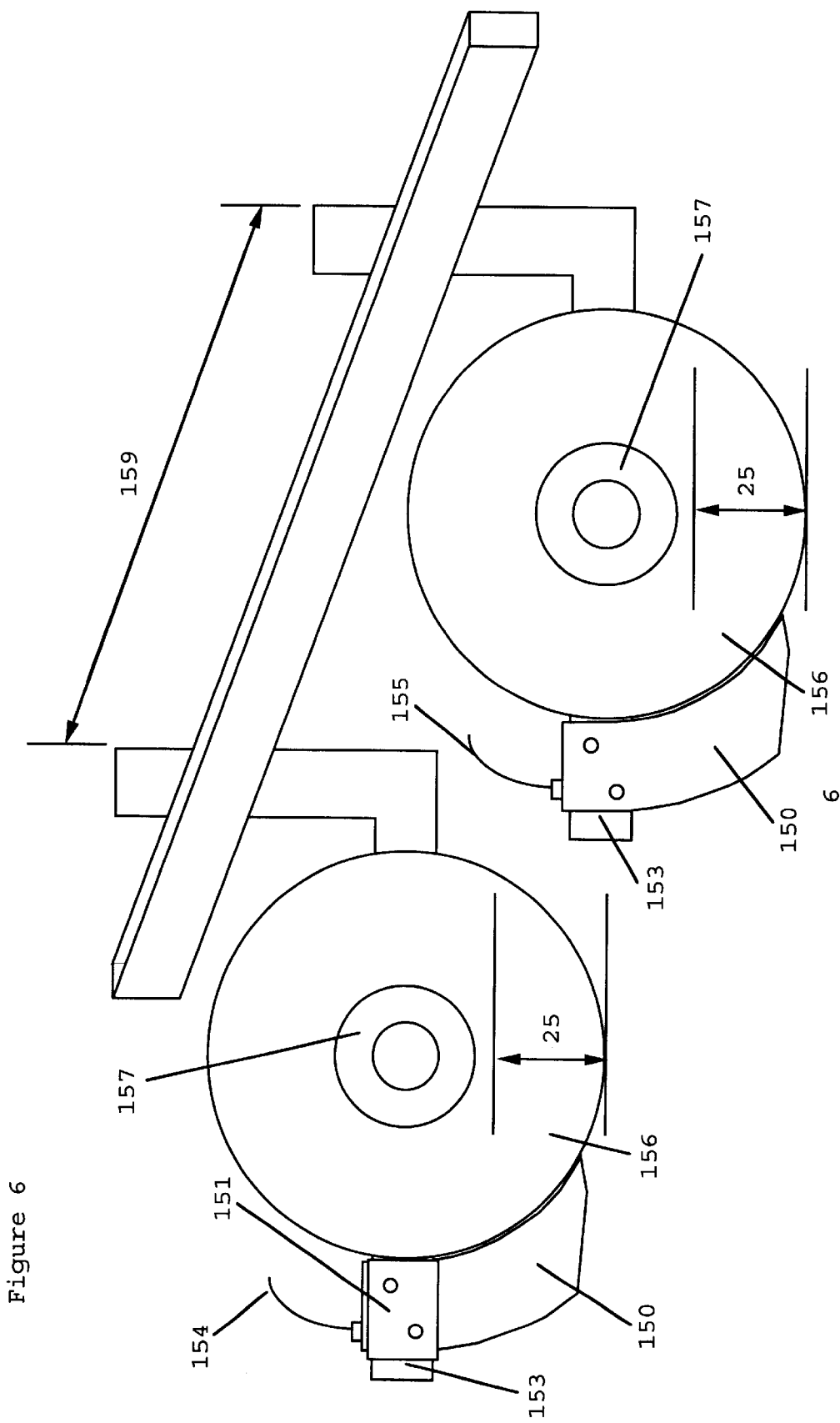
FIG. 6 illustrates an alternative embodiment of a separated two-electrode array wherein ground-engaging tool shanks trailing coulters serve as the electrodes.

Referring now to FIG. 6, a further alternative embodiment of a separated two-electrode array is illustrated in which standard ground-engaging tool shanks are operated in direction 6 at selected depth 25 trailing coulters separated by lateral distance 159 providing the two electrodes of the array for current flow laterally at depth in the earth. These configurations afford increased lateral and vertical interrogation proportional to electrode spacing 159. A first standard tool shank 150 is removably affixed to its attachment 153 but electrically insulated 151 from its attachment 153 and held at positive potential by control wiring 154 from control means 70. A second standard tool shank 150 is removably affixed to its attachment 153 and is held at ground potential by control wiring 155. It is preferable that when operated in conjunction with coulter 156 that hub insulation 157 be employed on coulter 156 in proximity to the insulated tool mount 151; optionally, coulter 156 may be insulated 157 at its hub from the second coulter 156 of the in situ soil resistivity array. Like-numbered elements depicted in this drawing are interchangeable.

Referring now to FIGS. 7A and 7B, embodiments of separated electrode arrays are disclosed using variations of the ground engaging elements and electrodes of FIG. 4, geometrically enhanced to increase the volume of soil interrogated in the direction of travel of the implement or laterally through use of a moving four electrode array. Such a configuration permits simultaneous multiple depths of interrogation.

In FIG. 7A, a first ground-engaging tool 132 as previously described in FIG. 4 is depicted along with electrode 130. The tool 132 is operated at a preselected depth 25 and is removably affixed to member 164 and operated in proximity to coulter 165. At a preselected distance 166 a second ground-engaging tool 161 is operated at a selected depth and its measuring electrode 163 is operated in the same direction of travel 6 as tool 132 and coulter 165. Tool 161 is removably affixed to member 164 and insulated therefrom by insulation 168. Control means 70 applies a positive potential to tool 161 via wiring 169 and applies ground potential via wiring 179 to tool 132. This causes a current to Flow in the earth between tool bodies 132 and 161. To provide improved accuracy of on-the-go measurement of complex in situ resistivity, sensing and control means 70 utilizes potential and current measurement means, FIG. 10, connected to wiring 169 and 170 to determine complex in situ resistivity soil values from electrodes 130 and 163.

In FIG. 7b, a first ground-engaging tool 180 of backswept geometry to shed debris from passage through residual crop detritus in the soil is removably affixed to support member 181. A second ground-engaging tool 182 of backswept geometry to shed debris is removably affixed to and insulated 184 from a second support member 183 which may be laterally or longitudinally separated from support member 181 by a distance 185, preferably 30 to 120 centimeters for row crops such as corn. Both tools are operated in direction 6 for complex in situ resistivity determinations. Sensing and control means 70 of FIG. 10 applies a positive potential to tool 182 via wiring 187 and applies ground potential via wiring 186 to tool 180. This causes a current to flow in the earth between tool bodies 180 and 182. To provide improved accuracy of on-the-go measurement of complex in situ resistivity, sensing and control means 70 utilizes potential and current measurement means 186 and 187 to determine complex in situ resistivity soil values from electrodes 188 and 189.

Referring now to FIG. 8, another embodiment of the methods of the present invention is shown providing multiple four electrode annular arrays each of which is radially attached to spokes 200 formed in a rotating wheel. As the wheel 205 rotates 201 in the direction of travel 6, each spoke probe 110 with adjustable electrode mounting and piercing point 20J is pressed into the soil to a selected depth 25, and slip ring means 216 connect wiring means 204 in the radial spokes to measuring circuitry in sensing and control means 70 by wiring means 212. Wiring 204 provides excitation from sensing and control means 70 and returns signals to sensing and control means 70. Outboard current electrodes 206 and 207 and inboard measuring electrodes 208 and 209 on each spoke probe 210 provide a separated and insulated 215 four electrode array for complex resistivity measurements of in situ soils by the further methods of this invention. Electrodes 206 through 208 on each spoke are, preferably flush with the surface of insulation 215. Electrodes 206 through 208 are further preferably annular rings and may be rotated as the electrodes wear to provide fresh flush surfaces for soil contact through adjustable point means 203. This rotating configuration affords minimal soil and crop disturbance and is particularly desirable for grasses, such as golf courses or lawns and drilled grain crops such as wheat.

Referring now to FIG. 9A, a removably affixed four electrode array 220 further illustrated in FIG. 9B is installed in a first flattened conduit 224 positioned in proximity to the heel 221 of a thin ground-engaging tool 223 by insulated adjustable spacer means 235 and operated at a predetermined depth 25 below the fracture zone 225 of tools 248 traveling through soil in direction 6 in advance of the electrode. This embodiment provides increased accuracy in local in situ measurements along the direction of tool travel, preferably in moist soils where lateral soil fracture by the passage of wobbling tools such as coulters is accentuated, and where an increase in the precision of local measurement of conductivity imbrued soils may be required.

Referring now to FIG. 9B, outboard current elements 227 and 228 and inboard measuring elements 229 and 230 of electrode array 220 provide a separated and insulated 215 four electrode array for complex resistivity measurements of local in situ soils by the further methods of this invention. Electrodes 227 through 230 of electrode array 220 are preferably flush with the surface of insulation 240 which is provided in "sandwich" construction between and outside the electrode elements. Electrodes 227 through 230 are further preferably solid metallic segments that wear from the bottom of the kerf cut in the soil to provide fresh flush surfaces for soil contact through adjustable spacer means 235 of FIG. 9B. Excitation and output signals from the four electrode array 220 communicate with sensing and control means 70 via conduit 224 protected wiring 236.

As has been described, complex resistivity values may be determined over various geometric distances, and the arrangement herein described provides localized determinations on the order of a few centimeters which permits this configuration the opportunity to achieve the enhanced calibration objects of the present invention. Preceding the electrode array 220 is an orifice 247 through which is periodically admitted by sensing and control means 70 sequential known conductivity fluids by means of second conduit 246 in tool 223 and from conduit 245 for purposes of local matrix resistivity calibration. For calibration, the complex in situ resistivity of a first soil sample in the presence of a first known conductivity solution is determined by the sensing and control means 70 and then the complex in situ resistivity of a second soil sample in the presence of a second known conductivity solution is determined by the sensing and control means 70. By means of sensing and control means 70, portions of the complete electrode array, but preferably electrodes 229 and 230, may be electrically connected within sensing and control means 70 to serve as positive potential measuring electrodes of an alternate array for concurrent macro measurements of lateral or longitudinal resistivity as previously described re FIGS. 7A–7B. For these purposes alternating current frequency separation means within sensing and control means 70 are employed to permit such concurrent measurement.

Other alternate forms of the present invention will suggest themselves from a consideration of the apparatus and practices hereinabove disclosed. Accordingly, it should be clearly understood that the systems and techniques described in the foregoing explanations and depicted in the foregoing drawings are intended as exemplary embodiments of the invention and not as limitations thereto.

What is claimed is:

1. A method for sensing substantially instantaneously at least one parameter of a soil while traversing a field of said soil, comprising the steps of:
   penetrating the soil of a first soil sample while traversing said sample, and
   pulsing said sample with a voltage differential or current pulse across said sample, and determining by transient analysis a parameter of said sample.

2. The method of claim 1, comprising the additional step of:
   determining a constituent of said soil related to the parameter determined while traversing said sample.

3. The method of claim 2, wherein said constituent of said soil sample and a spatial location of said soil sample are recorded.

4. The method of claim 3, further comprising the step of determining a prescription spatial treatment to be applied to said soil.

5. The method of claim 4, wherein said determined prescription spatial treatment and said spatial location are recorded.

6. The method of claim 4, further comprising the step of calibrating said prescription spatial treatment to be applied with means for relating spatial crop yield or quality to spatial constituents.

7. The method of claim 4, further comprising a variable rate treatment step of
   applying said spatial treatment to substantially said spatial location of said soil sample.

8. The method of claim 1, wherein the soil parameter determined is one of the parameters of soil conductivity, soil solution conductivity, soil particle conductivity or soil permitivity.

9. The method of claim 1, wherein said parameter of said soil sample and a spatial location of said soil sample are recorded.

10. A method for sensing, at least one parameter of a soil while traversing a field containing said soil, comprising the steps of
    penetrating the soil of a soil sample and sub-sample of said sample while traversing said sample,
    providing a current or voltage across said sample while traversing said sample, and
    determining a parameter of said soil.

11. The method of claim 10, wherein said determined parameter is one of the parameters of soil conductivity, soil solution conductivity, soil particle conductivity or soil permittivity.

12. The method of claim 10, wherein said current or voltage comprises an alternating current excitation wavefrom.

13. A method for sensing at least one parameter of a soil while traversing a field containing said soil, comprising the steps of:
    penetrating the soil of a soil sample and sub-sample of said sample while traversing said sample,
    providing a current or voltage across said sample,
    determining a parameter of said soil, and
    recording said parameter of said soil sample and a spatial location of said sample.

14. The method of claim 13, wherein said penetrating step is accomplished by a radial spoke probe of a rotatable wheel means.

15. The method of claim 13, further comprising the step of
    forming a four-electrode array for measuring potential across any pair of electrodes of said array.

16. The method of claim 13, wherein said soil sample is coupled by a second pair of insulated and electrically isolated electrodes connected to potential measuring means.

17. The method of claim 16, further comprising the step of
    enhancing said coupling by kerf closing means.

18. The method of claim 17, wherein said kerf closing means comprises a closing wheel or penetration depth hub.

19. The method of claim 16, wherein said electrodes comprise coulters aligned substantially laterally to each other.

20. The method of claim 19, wherein said second pair of coulter electrodes is arranged between said first pair of coulter electrodes.

21. The method of claim 13, further comprising the step of
    determining the spatial constituent of said soil related to said spatial parameter determined while traversing said soil.

22. The method of claim 21, wherein said spatial constituent determined is any of the constituents of nitrate, calcium, potassium, topsoil depth, water content, organic matter, cation exchange capacity, clay content, texture or soil type.

23. The method of claim 21, wherein said spatial constituent of said soil sample and a spatial location of said soil are recorded.

24. The method of claim 21, wherein said determination of said constituent comprises calibration information referenced by spatial location.

25. The method of claim 21, further comprising the step of
    determining a prescription treatment to be applied to said soil.

26. The method of claim 25, further comprising the step of
    recording said determined prescription treatment and a spatial location for said soil.

27. The method of claim 26, further comprising the step of
    calibrating said prescription spatial treatment to be applied with means for relating spatial crop yield or quality to spatial parameters.

28. The method of claim 27, further comprising a variable rate treatment of
    applying said spatial treatment to substantially said spatial location of said soil sample.

29. The method of claim 28, wherein said spatial treatment to be applied is any of the treatments of anhydrous ammonia, nitrogen in solution, manure, starter fertilizer, lime, potassium fertilizer, phosphate fertilizer or herbicide.

* * * * *